US011096975B2

(12) United States Patent
Mogna

(10) Patent No.: US 11,096,975 B2
(45) Date of Patent: Aug. 24, 2021

(54) COMPOSITIONS FOR USE IN THE TREATMENT OF TUMORS RESISTANT TO CHEMOTHERAPY

(71) Applicant: PROBIOTICAL S.P.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 15/555,920

(22) PCT Filed: Mar. 4, 2016

(86) PCT No.: PCT/IB2016/051216
§ 371 (c)(1),
(2) Date: Sep. 5, 2017

(87) PCT Pub. No.: WO2016/139625
PCT Pub. Date: Sep. 9, 2016

(65) Prior Publication Data
US 2018/0064774 A1   Mar. 8, 2018

(30) Foreign Application Priority Data
Mar. 5, 2015   (IT) .................. 102015902336226

(51) Int. Cl.
| A61K 8/60 | (2006.01) |
|---|---|
| A61K 36/28 | (2006.01) |
| A61K 31/136 | (2006.01) |
| A61K 31/337 | (2006.01) |
| A61K 31/365 | (2006.01) |
| A61K 31/4741 | (2006.01) |
| A61K 31/4745 | (2006.01) |
| A61K 31/513 | (2006.01) |
| A61K 31/519 | (2006.01) |
| A61K 31/555 | (2006.01) |
| A61K 31/675 | (2006.01) |
| A61K 31/704 | (2006.01) |
| A61K 31/7048 | (2006.01) |
| A61K 33/24 | (2019.01) |
| A61K 36/29 | (2006.01) |
| A61K 36/66 | (2006.01) |

(52) U.S. Cl.
CPC ............ *A61K 36/28* (2013.01); *A61K 31/136* (2013.01); *A61K 31/337* (2013.01); *A61K 31/365* (2013.01); *A61K 31/4741* (2013.01); *A61K 31/4745* (2013.01); *A61K 31/513* (2013.01); *A61K 31/519* (2013.01); *A61K 31/555* (2013.01); *A61K 31/675* (2013.01); *A61K 31/704* (2013.01); *A61K 31/7048* (2013.01); *A61K 33/24* (2013.01); *A61K 36/29* (2013.01); *A61K 36/66* (2013.01); *A61K 2300/00* (2013.01)

(58) Field of Classification Search
None
See application file for complete search history.

(56) References Cited

U.S. PATENT DOCUMENTS

| 6,426,351 | B1 | 7/2002 | Weichselbaum et al. |
|---|---|---|---|
| 9,757,405 | B2 * | 9/2017 | Frascini ............... A61K 31/664 |
| 10,195,219 | B2 | 2/2019 | Bent |
| 2011/0182943 | A1 * | 7/2011 | Kanwar .................. A23C 13/12 424/277.1 |
| 2013/0045179 | A1 * | 2/2013 | Ciustea .................. A61K 45/06 424/85.1 |
| 2014/0141082 | A1 * | 5/2014 | Gao ....................... A61K 31/05 424/474 |
| 2016/0213698 | A1 | 7/2016 | Frascini et al. |
| 2017/0209416 | A1 * | 7/2017 | Mogna .................. A61K 45/06 |

FOREIGN PATENT DOCUMENTS

| CN | 01/78783 A2 | 10/2001 |
|---|---|---|
| CN | 1470513 A | 1/2004 |
| CN | 1560265 A | 1/2005 |
| CN | 1911951 A | 2/2007 |
| CN | 2119434 A1 | 11/2009 |
| CN | 103608005 A | 2/2014 |
| EP | 1656939 A1 | 5/2006 |
| EP | 2119434 A1 * | 11/2009 |
| JP | 2005529123 A | 9/2005 |
| WO | 03/090681 A3 | 11/2003 |
| WO | 2006/032380 A1 | 3/2006 |
| WO | 2008/108647 A2 | 9/2008 |
| WO | 2010/001391 A1 | 1/2010 |
| WO | 2012/141575 A1 | 10/2012 |

(Continued)

OTHER PUBLICATIONS

Gautam R. et al. Rutin Attenuates Intestinal Toxicity Induced by Methotrexate Linked with Antioxidative and Antiinflammatory Effects. BMC Complementary & Alternative Medicine 16:1-6, 2016. (Year: 2016).*

Lissoni P. et al. Decreased Toxicity and Increased Efficacy of Cancer Chemotherapy Using the Pineal Hormone Melatonin in Metastatic Solid Tumour Patients with Poor Clinical Status. European J of Cancer 35(12)1688-1692, 1999. (Year: 1999).*

Duvoix, A., et al. "Effect of chemopreventive agents on glutathione S-transferase P1-1 gene expression mechanisms via activating protein 1 and nuclear factor kappaB inhibition." *Biochemical Pharmacology* 68, 1101-1111, (2004). 11 pages.

(Continued)

*Primary Examiner* — Ralph J Gitomer
(74) *Attorney, Agent, or Firm* — Steinfl + Bruno LLP

(57) ABSTRACT

The use of at least one flavonoid of natural or synthetic origin in association with cyclophosphamide and/or methotrexate to increase the effectiveness of chemotherapeutic treatments used in human and veterinary medicine for the treatment of tumors is described, in particular in case of resistance to the chemotherapeutic agents currently in use. At least one flavonoid herein described is selected from the group comprising or, alternatively, consisting of rutin, oxerutin, diosmin, troxerutin and hesperidin.

16 Claims, No Drawings

(56) References Cited

FOREIGN PATENT DOCUMENTS

| WO | 2015/036875 | 3/2015 |
|---|---|---|
| WO | 2016/009256 A1 | 1/2016 |

OTHER PUBLICATIONS

Jung, C. H., et al. "Anti-asthmatic Action of Quercetin and Rutin in Conscious Guinea-pigs Challenged with Aerosolized Ovalbumin." *Archives of Pharmacal Research* 30(12), 1599-1607, (2007). 9 pages.

Takasaki, M., et al. "Anti-tumor-promoting activity of lignans from the aerial part of *Saussurea medusa*." Cancer Letters 158, 53-59, (2000). 7 pages.

Tang, W., et al. "Recent Development of Antitumor Agents from Chinese Herbal Medicines; Part I. Low Molecular Compounds." *Planta Med* 69, 97-108, (2003). 12 pages.

Yarnell, E., et al. "Can Botanicals Reduce Multidrug Resistance in Cancer?" *Alternative & Complementary Therapies* 8(6), 336-340, (2002).

International Preliminary Report on Patentability for International Application No. PCT/IB2014/063187 filed Jul. 17, 2014 on behalf of Probiotical S.P.A. dated Mar. 15, 2016. 5 pages.

International Preliminary Report on Patentability (IPRP) for International Application No. PCT/IB2016/051216 filed Mar. 4, 2016 on behalf of Probiotical S.P.A. dated Sep. 5, 2017. 7 pages. (English Only).

International Search Report and Written Opinion for International Application No. PCT/IB2014/063187 filed Jul. 17, 2014 on behalf of Probiotical S.P.A. dated Dec. 18, 2014. 7 pgs.

International Search Report and Written Opinion for International Application No. PCT/IB2016/051216 filed Mar. 4, 2016 on behalf of Probiotical S.P.A. dated Jun. 2, 2016. 12 pgs.

Ahmad, et al. "Differential Antiproliferative and Apoptotic Response of Sanguinarine for Cancer Cells versus Normal Cells", Clinical Cancer Research, 2000, vol. 6, pp. 1524-1528.

Awale et al. "Identification of Arctogenin as an Antitumor Agent Having the Ability to Eliminary the Tolerance of Cancer Cells to Nutrient Starvation", Cancer Research, Feb. 1, 2006, vol. 66 (3), pp. 1751-1757.

Bourogaa et al. "Hammada scoparia flavonoids and rutin kill adherent and chemoresistance leukemic cells" Leukemia Research; vol. 35; 2011; pp. 1093-1101.

El-Readi, et al., "Inhibition of P-glycoprotein activity by limonin and other secondary metabolites from *Citrus* species in human colon and leukaemia cell lines", European Jounral of Pharmacology, 626, 2010, pp. 139-145.

Febriansah, et al. "Hesperidin as a preventive resistance agent in MCF-7 breast cancer cells line resistance to doxorubicin", Asian Pacific Journal of Tropical Biomedicine, 2014, vol. 4 (3), pp. 228-233.

Fojo et al. "Mechanisms of Resistance to PARP Inhibitors—Three and Counting" Cancer Discovery 3(1); Jan. 2013; pp. 20-23.

Guardia et al. "Anti-inflammatory properties of plant flavonoids. Effects of rutin, quercetin and hesperidin on adjuvant arthritis in rat" Il Farmaco; vol. 56; 2001; pp. 683-687.

Hanachi et al. "Cytotoxic Effect of *Berberis vulgaris* Fruit Extract on the Proliferation of Human Liver Cancer Cell Line (HepG2) and its Antioxidant Properties" International Journal of Cancer Research; vol. 2; No. 1; 2006; pp. 1-9.

Hirose et al. "Effects of arctiin on PhIP-induced mammary, colon and pancreatic carcinogenesis in female Sprague-Dawley rats and MeIQx-induced hepatocarcinogenesis in male F344 rats", Cancer Letters, vol. 155, 2000, pp. 79-88.

Jantova et al., "Berberine induces apoptosis through a mitochondrial-caspase pathway in human promonocytic U937 cells", Toxicology in Vitro, vol. 21, 2007, pp. 25-31.

Luo et al. "Inhibition of Cell Growth and VEGF Expression in Ovarian Cancer Cells by Flavonoids" Nutrition and Cancer; vol. 60; No. 6; 2008; pp. 800-809.

Malikova et al. "The effect of chelerythrine on cell growth, apoptosis, and cell cycle in human and normal cancer cells in comparison with sanguinarine" Cell Biol. Toxlicol. 2006, vol. 22, pp. 439-453.

Mani et al. "Insilico Analysis on the Effect of Rutin Bioflavonoid and Chemotherapeutic Drug Cyclophosphamide on Nuclear Factor Kappa-B Protein Expression" International Journal of Pharma and Bio Sciences. vol. 5; No. 1; Jan. 2014; pp. B-560-B-569.

Metodiewa et al. "Evidence for Antiradical and Antioxidant Properties of Four Biologically Active N,N-Diethylaminoethyl Ethers of Flavanone Oximes: A Comparison with Natural Polyphenolic Flavonoid (Rutin) Action" Biochemistry and Molecular Biology International; vol. 41; No. 5; Apr. 1997; pp. 1067-1075.

Navarro-Nunez et al. "Apigenin Inhibits Platelet Adhesion and Thrombus Formation and Synergizes with Aspirin in the Suppression of the Arachidonic Acid Pathway" Journal of Agricultural and Food Chemistry; 2008; 8 pages.

Potdar et al. "Phyto-chemical and pharmacological applications of *Berberis aristata*", Fitoterapia, vol. 83, 2012, pp. 817-830.

Tamaki et al. "Inhibitory Effects of Herbal Extracts on Breast Cancer Resistance Protein (BCRP) and Structure-Inhibitory Potency Relationship of Isoflavonoids", Drug Metabolism and Pharmcokinetics, vol. 25, No. 2, Jan. 1, 2010, pp. 170-179.

Wang, et al. "Suppression of growth, migration and invasion of highly-metastatic human breast cancer cells by berbamine and its molecular mechnisms of action" Molecular Cancer, 2009, vol. 8; 81, 15 pgs.

Webster, et al., Protective effect of rutin, a flavonol glycoside, on the carcinogen-induced DNA damage and repair enzymes in rats, Cancer Letter, 1996, vol. 109, pp. 185-191.

Non-Final-Office Action for U.S. Appl. No. 14/917,939, filed Mar. 9, 2016 on behalf of Probiotical S.P.A. dated Jan. 12, 2017. 17 pgs.

Notice of Allowance for U.S. Appl. No. 14/917,939, filed Mar. 9, 2016 on behalf of Probiotical S.P.A. dated Jul. 3, 2017. 10 pgs.

Osol, A., et al., *Remington's Pharmaceutical Sciences, 15th Edition*. Mack Publishing Company, Easton PA, 1975.

Japanese Office Action for Japanese Patent Application No. 2017-546598 on behalf of Probiotical S.P.A dated Jan. 7, 2020, 5 pages. Japanese + English translation.

Russian Office Action for RU application No. 2017132516 filed on Mar. 4, 2016 on behalf of Hoffmann-Eitle SRL. dated Sep. 2, 2019. Russian & English Trans. 16 Pages.

Russian Search Report for RU application No. 2017132516 filed on Mar. 4, 2016 on behalf of Hoffmann-Eitle SRL. dated Sep. 2, 2019. Russian & English Trans. 4 Pages.

Alonso Castro, et al., "Rutin exerts antitumor effects on nude mice bearing SW480 tumor", Archives of Medical Research 44, 2013, 346-351.

Chinese Office Action and Search Report for CN Appl. No. 2016800130286 filed on Mar. 4, 2016 on behalf of Probiotical S.P.A. dated Apr. 24, 2020. Plus English translation. 21 Pages.

Communication pursuant to Article 94(3) received for EP App. No. 16718006.6 filed on Mar. 4, 2016 on behalf of Probiotical S.P.A. dated Feb. 12, 2020. 7 Pages.

Cutando, et al., "Role of Melatonin in Cancer Treatment", Anticancer Research , 32: 2747-2753 (2012).

Di Bella G. et al., The Di Bella Method (DBM) in the treatment of prostate cancer: a preliminary retrospective study of 16 patients and a review of the literature. Neuro Endocrin Lett., 2013, 34(6): 523-528, PMID: 24378460.

Gambashidze K. et al., Antitumor and adjuvant effects of phagelysates of *E. coli* in mice with Ehrlich carcinoma. Exp. Oncol. Jul. 2012, 34(2): 107-111, PMID: 23013762.

Indian Office Action for IN Application No. 201747032728 filed on Sep. 15, 2017 on behalf of Probiotical S.P.A. dated Jul. 13, 2020. 7 Pages. Hindi and English.

International Preliminary Report on Patentability for International Application No. PCT/IB2015/000284 filed Mar. 5, 2015 on behalf of Brobiotical S.P.A.. dated Jan. 17, 2017. 9 pages.

(56) References Cited

OTHER PUBLICATIONS

International Search Report and Written Opinion for International Application No. PCT/IB2015/000284 filed Mar. 5, 2015 on behalf of Probiotical S.P.A. dated Jul. 10, 2015. 15 pages.
Italian Application MI2014A001308 filed on behalf of Probiotical S.P.A./ Mogna. Filed on Jul. 17, 2014. Made available under the PCT on Feb. 8, 2016. Italian with English translation. 39 Pages.
Italian priority Application No. MI2014A001308 filed on Jul. 17, 2014 on behalf of Probiotical S.P.A. Certified English translation dated Feb. 7, 2020. (19 pages).
Italian Search Report and Written Opinion for Italian Patent Application No. ITMI20141308 filed Jul. 17, 2014 on behalf of Probiotical S.P.A. dated Dec. 10, 2014. 7 pages (Italian original + English translation).
Japanese Office Action Application No. 2017-502689 delivered Jan. 8, 2019 for applicant Probiotical S.P.A , dated Jan. 8, 2019. 11 pages. (Original + English translation).
Jung, et al., "Melatonin in Cancer Management: Progress and Promise", Cancer Res, 2006, 66: (20), 9789-9793, Oct. 15, 2006.
Martin et al., "Melatonin-induced methylatin of the ABCG2/BCRP promoter as a novel mechanism to overcome multidrug resistance in brain tumour stem cells", British Journal of Cancer, 203, 108, 2005-2012. (Year: 2013).
Nazari et al. "Inactivation of Nuclear Factor-kB by citrus flavanone hesperidin contributes to apoptosis and chemo-senitizing effect in Ramos cells", *European Journal of Pharmacology* 650, 526-533 (Year: 2011).
Non-Final Office Action for U.S. Appl. No. 15/326,627, filed Jan. 16, 2017 on behalf of Probiotical S.P.A. dated Aug. 29, 2019 19 pages.
Non-Final Office Action for U.S. Appl. No. 15/326,627, filed Jan. 16, 2017 on behalf of Probiotical S.P.A. dated Jun. 19, 2020.18 pages.
Office Action for Japanese patent application No. JP 2017-502689, dated Jan. 7, 2020, 6 pages (with English translation).
Office Action for Russian Application No. 2017102705/15(004708) filed on Mar. 5, 2015 on behalf of Probiotical S.P.A., IT. dated Jul. 27, 2018. 18 pages (Russian + English translation).
Park, S.Y. et al., Sanguinarine inhibits invasiveness and the MMP-9 and COX-2 expression in TPA-induced breast cancer cells by inducing HO-1 expression. Oncol Rep., Jan. 2014, 31(1): 497-504, PMID: 24220687.
Raza H. et al., Alterations in mitochondrial respiratory functions, redox metabolism and apoptosis by oxidant 4-hydroxynonenal and antioxidants curcumin and melatonin in PC12 cells. Toxicol Appl Pharmacol., Jan. 15, 2008; 226(2): 161-168, PMID: 17935746.
Russian Office Action for RU Application No. 2017132516 filed on Mar. 4, 2016 filed on behalf of Probiotical S.P.A. dated Mar. 11, 2020. Original + English Translation. 13 Pages.
Search Report for Russian Application No. 2017102705/15(004708) filed on Mar. 5, 2015 on behalf of Probiotical S.P.A., IT. dated Jul. 27, 2018. 5 pages (Russian + English translation).
Srinivasan, et al, "Therapeutic Actions of Melatonin in Cancer: Possible Mechanisms", Integrative cancer therapies, 2008, 7(3), 189-203.
Yao et al. "Arctigenin Enhances Chemosensitivity of Cancer Cells to Cisplatin Through Inhibition of STAT3 Signaling Pathway", *Journal of Cellular Biochemistry*, 112:2837-2849.(Year: 2011).
Yun, et al., "Melatonin sensitizes H1975 Non-Small-Cell Lung Cancer Cells Harboring a T790M-Targeted Epidermal Growth Factor Receptor Mutation to the Tyrosine Kinase Inhibitor Gefitinib", Cellular Physiology and Biochemistry, vol. 34, No. 3, Jan. 1, 2014, pp. 865-872.
Office Action (Reasons for Refusal) for Japanese application No. 2017-502689 filed in the name of Probiotical S.P.A. dated Sep. 1, 2020. 5 pages. Original and English translation.
Russian Office Action for RU2017132516 filed on Mar. 4, 2016 in the name of Probiotical S.p.A., IT. dated Jul. 23, 2020. Original+ Eng. 16 pages.
Communication pursuant to Article 71 (3) received for EP App. No. 16718006.6 filed on Mar. 4, 2016 on behalf of Probiotical S.P.A. dated Oct. 20, 2020. 27 Pages.
Communication pursuant to Article 94(3) received for EP App. No. 15715813.0 filed on Mar. 5, 2015 on behalf of Probiotical S.P.A. dated Dec. 16, 2020. 4 Pages.
Communication pursuant to Article 94(3) received for EP App. No. 15715813.0 filed on Mar. 5, 2015 on behalf of Probiotical S.P.A. dated Feb. 17, 2020. 5 Pages.
Communication pursuant to Article 94(3) received for EP App. No. 15715813.0 filed on Mar. 5, 2015 on behalf of Probiotical S.P.A. dated Sep. 18, 2018. 7 Pages.
Communication pursuant to Article 71 (3) received for EP App. No. 14766538.4 filed on Jul. 17, 2014 on behalf of Probiotical S.P.A. dated May 11, 2018. 45 Pages.
Japanese Office Action for Japanese Patent Application No. 2017-546598 on behalf of Probiotical S.P.A dated Oct. 20, 2020, 7 pages. Japanese +English translation.
Search Report & Written Opinion for IT MI20131495 filed on September 10, 2013. Dated Dec. 12, 2013. 8 Pages.
Search Report & Written Opinion for IT MI20150332 filed on Mar. 5, 2015 on behalf of Probiotical S.P.A. dated Nov. 5, 2015. 9 Pages.
Simmons, J.K et al. Animal Models of Bone Metastasis. Veterinary Pathology, 2015, vol. 52 (5), 827-841.
Communication pursuant to Article 94(3) received for EP App. No. 14766538.4 filed on Jul. 17, 2014 on behalf of Probiotical S.P.A. dated Oct. 20, 2017. 6 Pages.
Altgelt, Johanna "Breast Cancer, Chemotherapy, & Antioxidants" from URL:pinestreetfoundation.org/breast-cancer-chemotherapy-antioxidants/} Pine Street Foundation, Sep. 23, 2007. Retrieved online Feb. 17, 2021.17 Pages.
Decision to Grant for Japanese Application No. 2017-502689 delivered Jan. 8, 2019 for applicant Probiotical S.P.A. Mailing Date: Jan. 12, 2021. 4 pages. (Original + English translation).
Kashif M, et al. "Cytotoxic and antioxidant properties of phenolic compounds from Tagetes patula flower" Pharmaceutical Biology, Dec. 24, 2014,53(5), pp. 672-681, doi: 10.3109/13880209.2014. 936471. 11 Pages.
Notice of allowance for U.S. Appl. No. 15/326,627, filed Jan. 16, 2017, on behalf of Probiotical S.P.A. Mail Date: Feb. 26, 2021. 26 Pages.
Yi C, et al. "Melatonin Enhances the Anti-Tumor Effect of Fisetin by Inhibiting COX-2/iNOS and NF-kB/p300 Signaling Pathways", PLoS ONE, 2014, 9(7): e99943; doi: 10.1371/journal.pone. 0099943. 11 Pages.

* cited by examiner

COMPOSITIONS FOR USE IN THE TREATMENT OF TUMORS RESISTANT TO CHEMOTHERAPY

CROSS REFERENCE TO RELATED APPLICATIONS

The present application is the U.S. national stage of International Patent Application PCT/IB2016/051216 filed internationally on Mar. 4, 2016, which, in turn, claims priority to Italian Patent Application No. 102015902336226 filed on Mar. 5, 2015.

SUMMARY OF THE INVENTION

The present invention relates to the use of at least one flavonoid of natural or synthetic origin in association with cyclophosphamide and/or methotrexate to increase the effectiveness of chemotherapeutic treatments used in human and veterinary medicine for the treatment of tumors, in particular in case of resistance to the chemotherapeutic agents currently in use; said at least one flavonoid is selected from the group comprising or, alternatively, consisting of rutin, oxerutin, diosmin, troxerutin and hesperidin.

BACKGROUND ART

At present, the resistance of tumor cells to chemotherapeutic treatments represents a problem of enormous proportions and in continuous evolution. Drug resistance manifests itself both in solid tumors and in tumors of the lymphatic system, and can occur from the very start of a treatment, or arise subsequently, after an initial positive response to the treatment: Very often, for example, chemoresistance manifests itself during a treatment of relapsing tumors. An even more serious problem is multiple chemoresistance, i.e. the occurrence, after treatment with a given chemotherapeutic agent, of resistance against other chemotherapeutic agents.

The most accredited hypotheses concerning the origin of chemoresistance, which manifests itself in the majority of tumors that initially respond to chemotherapeutic treatment, suggest that drug resistance is the result of a series of mutations at the level of the tumor cells, the ability of tumor cells to "learn" to metabolize the chemotherapeutic agents, repair chemotherapy-induced damage to DNA and prevent chemotherapy-induced apoptosis.

One approach for trying to overcome the problem of chemoresistance is therapy combining different types of chemotherapeutic agents: however, in this case as well, the results are not satisfactory, and indeed multiple resistance against various chemotherapeutic agents occurs with growing and alarming frequency. Notwithstanding research and the continuous development of new drugs, to be used also in combination, the problem of chemoresistance persists and is apparently inevitable, given the malleable nature of cancer cells [Fojo T. and Bates S., Cancer Discov; 3(1); 20-3, 2012].

Consequently, there is a very great need to overcome this problem.

Flavonoids are polyphenolic compounds, secondary metabolites of plants. They are usually present in the plant as glycosides and in the same plant anaglycone can exist in combination with different sugars. Preferably, the flavonoids of the present invention are selected from the group comprising or, alternatively, consisting of rutin, oxerutin, diosmin, troxerutin and hesperidin.

Oxerutin has demonstrated to be useful in favoring elasticity and decreasing capillary permeability, thus favoring a physiological improvement in microcirculation and a reduction in the formation of edema.

Hesperidin is a glycosylated fiavanone, a type of flavonoid that is found above all in citrus fruit. It is particularly abundant in the peel and pulp of such fruit. Its aglycone is called hesperetin. Hesperidin has demonstrated to be a valid vasoprotector and increases the efficiency of collagen and of connective tissue.

Diosmin is a semisynthetic molecule (modified starting from a hesperidin), belonging to the family of flavonoids. It is a phlebotropic drug used as a vasoprotector in all pathologies which show a deficiency in the structures of blood vessels, for example in chronic venous insufficiency and acute and chronic hemorrhoidal disease, and as an adjuvant therapy after hemorrhoidectomy.

Troxerutin ($C_{33}H_{42}O_{19}$, molecular mass 742.68 g/mole) is a flavonol (also known as vitamin P4), in particular it is a hydroxyethyl rutoside which is extracted for example from *Styphnoiobium japonicum* and is present also in tea, coffee, cereals and in many types of fruit and vegetables. It belongs to a group of molecules, rutosides, used for the treatment of edema caused by venous insufficiency. Troxerutin has the property to reduce the filtration capacity at capillary level. Troxerutin is used as a vasoprotector in pathologies involving capillary fragility.

Rutin (commonly also known as rutoside), whose chemical name is 2-(3,4-dihydroxyphenyl)-4,5-dihydroxy-3-{3,4,5-trihydroxy-6-[(3,4,5-trihydroxy-6-methyl-oxan-2-yl)oxymethyl}oxan-2-yl]oxy-chromen-7-one, is a flavonoid glycoside consisting of the aglycone quercetin (a flavonol) bonded to the disaccharide rutinose.

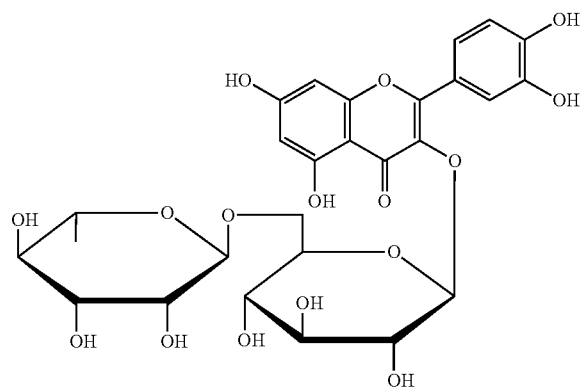

Rutin is found in nature in numerous plants, in particular plants of the genera *Citrus* and *Rheum* (rhubarb), in buckwheat, in red wine, in asparagus, in peppermint, in eucalyptus, and in many berries such as cranberries (*Vaccinium macrocarpon*) and mulberries.

The reinforcing effect of rutin on the wall of capillaries, and more generally its beneficial action on microcirculation, is exploited for the treatment of hemorrhoids and hematomas.

Recent studies have highlighted the pharmacological properties of rutin, in particular its anti-aggregation activity on platelets [Navarro-Nùñez et al. (2008); J. Agric. Food Chem. 56 (9): 2970-6]; its anti-inflammatory activity [Guardia et al. (2001); Il Farmaco 56 (9): 683-7; Chan Hun Jung et al. (2007); Arch, Pharmacal Research 30 (12): 1599-1607]; and antioxidant activity [Metodiewa et al. (1997); IUBMB Life 41 (5); 1067].

In vitro studies have demonstrated that rutin is capable of inhibiting the vascular endothelial growth factor, thus acting as an angiogenesis inhibitor [Luo et al. (2008); Nutrition and Cancer 60 (6); 800-9].

Recently, Boutogaa et al. [Leukemia Research 35(2011) 1093-1101] described that an extract of *Hammada scoparia*, containing rutin, is capable of inducing apoptosis in adhering leukemia cells: EP 2 119 434 describes the use of rutin for the treatment of acute myeloid leukemia, for preventing tumor relapse and/or for preventing the occurrence of solid tumor metastasis. No effects of rutin on tumor cells resistant to chemotherapeutic agents are reported.

Publication WO2001/078783 describes anti-tumor compositions comprising quercetin and numerous extracts of medicinal plants, but no reference is made to the activity against chemoresistant cells.

DESCRIPTION OF THE INVENTION

It has indeed been found that the compounds rutin, oxerutin, diosmin, troxerutin and hesperidin re-establish the sensitivity to chemotherapeutic treatment of resistant tumor cell lines, preferably cell lines of breast cancer in women.

The present invention relates to a composition for use in the treatment resistant to chemotherapy, comprising a mixture which comprises or, alternatively, consists of at least one flavonoid and at least one chemotherapeutic agent selected from the group comprising or, alternatively, consisting of rutin, oxerutin, diosmin, troxerutin and hesperidin and at least one chemotherapeutic agent:

In a preferred embodiment, said chemotherapeutic agent is selected from the group comprising or, alternatively, consisting of cyclophosphamide, 5-flurouracyl, methotrexate, platinum complexes (cisplatin, oxaliplatin, carboplatin, etc.), taxanes, doxorubicin, epirubicin and mitoxantrone. Advantageously, said flavonoid is rutin and said chemotherapeutic agent is cyclophosphamide and/or methotrexate.

Therefore, an object of the present invention is a composition for use in the treatment of tumors resistant to chemotherapy, comprising a mixture which comprises or, alternatively, consists of rutin, cyclophosphamide and/or methotrexate.

The present invention also relates to a composition comprising a mixture which comprises or, alternatively, consists of at least one flavonoid selected from the group comprising or, alternatively, consisting of rutin, oxerutin, diosmin, troxerutin and hesperidin, preferably rutin; and chemotherapeutic agents, preferably cyclophosphamide and/or methotrexate, for use as an adjuvant to chemotherapeutic agents for the treatment of tumors resistant to chemotherapy, that is, to increase the effectiveness of chemotherapeutic treatments used in human and veterinary medicine for the treatment of tumors, preferably solid tumors, in particular in case of resistance to the chemotherapeutic agents currently in use. Advantageously, the use of said composition as an adjuvant makes it possible to reduce the daily doses used and the daily amount of chemotherapeutic agents to be administered.

A solid tumor consists of a compact mass of tissue which grows and differs from a liquid tumor consisting of cells in suspension. Solid tumors have a specific structure resembling that of a healthy tissue and comprise two mutually dependent portions: the parenchyma and the stroma. In some solid tumors (including those originating from epithelial cells) there is a basal lamina separating the block of tumor cells from the stroma; however, this basal lamina is often incomplete. Though solid tumors represent the majority of human tumors, little is known about the genetic and chromosomal mutations which characterize them; firstly, because it is very difficult to obtain satisfactory chromosomal preparations from malignant tissues and, secondly, because the karyotype of these tumor cells often exhibits strange chromosomes in large numbers. This makes it difficult to distinguish the primary genetic changes from those occurring later, when the tumor phenotype is fully evolving. Despite these difficulties, however, new techniques of cell culture, chromosome banding and hybridization, such as CGH (Comparative genomic hybridization), FISH (Fluorescent in situ hybridization) and SKY (Spectral karyotyping) have contributed to a noteworthy increase in the molecular characterizations of cytogenetic anomalies encountered in solid tumors. These techniques have revealed substantial chromosomal rearrangements in tumor cells and the close association among specific chromosomal changes and particular types of solid tumors, above all mesenchymal tumors. Many of the genes involved have been cloned and analyzed, even if our knowledge is still limited. Neoplastic cells are divided into benign and malignant; both types of cells are further divided, according to the tissue of origin, into mesenchymal, epithelial, nervous system, embryonal and germinal tumor cells. Alongside these tumors there are also those of unknown cytologic origin.

Another object of the present invention is a composition for use in the treatment of chemoresistant tumors, preferably in the treatment of breast cancer in women, comprising a mixture which comprises or, alternatively, consists of: (i) at least one flavonoid selected from the group comprising or, alternatively, consisting of rutin, oxerutin, diosmin, troxerutin and hesperidin; (ii) at least one chemotherapeutic agent; and (iii) at least one compound selected from the group comprising or, alternatively, consisting of arctigenin, arctiin, berberine, berbamine, sanguinarine and chelerythrine, as such or in the form of plant extracts containing said compounds. Advantageously, said mixture comprises cyclophosphamide and/or methotrexate and extracts of arctigenin, arctiin, berberine, berbamine, sanguinarine and chelerythrine.

The invention thus also relates to associations of at least one flavonoid, preferably selected from the group comprising or, alternatively, consisting of rutin, oxerutin, diosmin, troxerutin and hesperidin, with substances having an anti-tumor activity, said associations being in a form that is also suitable for the separate or sequential administration of the flavonoid and chemotherapeutic agents.

Said at least one flavonoid is selected from the group comprising or, alternatively, consisting of rutin, oxerutin, diosmin, troxerutin and hesperidin and can be used, according to the invention, in association with all known chemotherapeutic agents, said chemotherapeutic agents used either alone or in associations in chemotherapy protocols, in particular for the treatment of solid tumors. Examples of such chemotherapeutic agents comprise or, alternatively, consist of cyclophosphamide, 5-fluoruracyl, methotrexate, platinum complexes (cisplatin, oxaliplatin, carboplatin, etc.), taxanes, doxorubicin, epirubicin and mitoxantrone. In one embodiment, the at least one compound selected from the group comprising or, alternatively, consisting of rutin, oxerutin, diosmin, troxerutin and hesperidin is in association with chemotherapeutic agents which comprise or, alternatively, consist of cyclophosphamide in order to restore or increase sensitivity to chemotherapeutic treatment of resistant tumor cell lines, or for the treatment of tumors, preferably for the treatment of solid tumors. In one preferred embodiment, the at least one compound selected from the group comprising or, alternatively, consisting of rutin, oxerutin, diosmin, troxerutin and hesperidin is in association with chemotherapeutic agents which comprise or, alternatively, consist of cyclophosphamide and methotrexate in order to restore or increase sensitivity to chemotherapeutic treatment of resistant tumor cell lines, or for the treatment of tumors, preferably for the treatment of solid tumors. Preferably, rutin is used in association with cyclophosphamide and methotrexate.

According to another aspect of the present invention, the invention relates to compositions comprising: (i) at least one flavonoid, preferably selected from the group comprising or, alternatively, consisting of rutin, oxerutin, diosmin, troxerutin and hesperidin; (ii) at least one chemotherapeutic agent selected from the group comprising or, alternatively, consisting of cyclophosphamide, 5-fluoruracyl, methotrexate, platinum complexes (cisplatin, oxaliplatin, carboplatin, etc.), taxanes, doxorubicin, epirubicin and mitoxantrone; and/or (iv) at least one alkaloid selected from among Berberidaceae and/or Papavaeraceae and/or lignans from Asteraceae, *Harpagophytum procumbens*.

According to another aspect of the present invention, the invention relates to compositions comprising at least one flavonoid, preferably selected from the group comprising or, alternatively, consisting of rutin, oxerutin, diosmin, troxerutin and hesperidin in association with at least one alkaloid selected from among Berberidaceae and/or Papavaeraceae and/or lignans from Asteraceae.

The compositions of the present invention can further contain a compound selected from the group comprising or, alternatively, consisting of natural or synthetic substances, these substances being selected from the group comprising or, alternatively, consisting of apigenin, asparagus (ursolic acid), curcumin, lycopene, chili pepper (capsaicin), resveratrol, green tea (Cameilin B) and *Uncaria* sspp.; and/or melatonin; preferably melatonin.

In particular, the compositions of the invention preferably contain the lignans arctigenin and/or arctiin, the alkaloids berberine, and/or berbamine, and/or sanguinarine, and/or chelerythrine; or else the compositions of the invention preferably contain the lignans arctigenin and/or arctiin, the alkaloids berberine, and/or berbamine, and/or sanguinarine, and/or chelerythrine; and/or a compound selected from the group comprising or, alternatively, consisting of natural or synthetic substances, these substances being selected from the group comprising or, alternatively, consisting of apigenin, asparagus (ursolic acid), curcumin, lycopene, chili pepper (capsaicin), resveratrol, green tea (Camellin B) and *Uncaria* sspp.; and/or melatonin; preferably melatonin.

According to another aspect of the present invention, the invention relates to compositions comprising or, alternatively, consisting of: (i) at least one flavonoid, preferably selected from the group comprising or, alternatively, consisting of rutin, oxerutin, diosmin, troxerutin and hesperidin; and at least one alkaloid selected from the group comprising or, alternatively, consisting of arctigenin, arctiin, berberine, berbamine, sanguinarine, chelerythrine and *harpagophytum procumbens* (devil's claw, which inhibits the growth of PEG2), as such or in the form of plant extracts containing said compounds.

According to another embodiment, the invention relates to compositions comprising or, alternatively, consisting of: (i) at least one flavonoid, preferably selected from the group comprising or, alternatively, consisting of rutin, oxerutin, diosmin, troxerutin and hesperidin; (ii) at least one chemotherapeutic agent selected from the group comprising or, alternatively, consisting of cyclophosphamide, 5-fluoruracyl, methotrexate, platinum complexes (cisplatin, oxaliplatin, carboplatin, etc.), taxanes, doxorubicin, epirubicin and mitoxantrone; and (iv) at least one compound selected from the group comprising or, alternatively, consisting of arctigenin, arctiin, berberine, berbamine, sanguinarine and chelerythrine, as such or in the form of plant extracts containing said compounds. Preferably, the composition comprises rutin, cyclophosphamide, methotrexate, arctigenin, arctiin, berberine, berbamine, sanguinarine and chelerythrine.

Preferably, the compositions of the present invention further comprise at least one compound selected from the group comprising or, alternatively, consisting of apigenin, asparagus (ursolic acid), curcumin, lycopene, chili pepper (capsaicin), resveratrol, green tea (Camellin B), *Uncaria* sspp. and melatonin.

The compositions of the invention are particularly useful for the prevention and/or treatment of neoplasias and for the prevention/suppression of chemoresistance to antiblastics and/or radioresistance to radiotherapy.

The compositions of the invention are particularly useful as adjuvants to chemotherapeutic agents for the treatment of tumors resistant to chemotherapy, preferably solid tumors.

The compositions of the invention are particularly useful for increasing the effectiveness of chemotherapeutic treatments used in human and veterinary medicine for the treatment of the tumors, in particular in case of resistance to the chemotherapeutic agents currently in use.

The Applicant has surprisingly found that the flavonoids of the present invention increase the anti-tumor activity of traditional chemotherapeutic agents and reduce the resistance of tumor cells to drugs. Therefore, an object of the present invention consists in providing a composition for use in the treatment of tumors, which enables to maximize the effects of conventional chemotherapeutic agents, reducing their dose of administration and as a result their adverse effects on patients.

The compositions of the present invention significantly reduce the cell viability of chemoresistant human tumor cells.

In virtue of the above, the compositions of the present invention can be effectively used not only to treat tumors that have already developed chemoresistance, but also to prevent the development of chemoresistance by tumor cells and the formation of metastases.

Therefore, one object of the present patent application is to provide a chemotherapeutic treatment that is more effective in treating chemoresistant tumors than the treatments generally used in medicine, which makes it possible to reduce the amount of chemotherapeutic drugs necessary in the treatment of tumors, in particular in the case of chemoresistant tumors, and which can be useful for preventing the development of chemoresistance and the formation of metastases.

Plants belonging to the family of Asteraceae (*Arctium lappa, Cnicus benedictus* and *Saussurea medusa* or other species of *Saussurea*) are characterized by their content of arctigenin and arctiin, molecules already known for their anti-tumor action. The use of extracts of *Arctium lappa* in cancer therapy and prophylaxis is described, for example, in CN 1560265. The use of *Saussurea* as an anti-tumor agent is described, for example, in patent application WO 2006 032380. The anti-tumor activity of lignans extracted from aerial parts of *Saussurea medusa* was described in Cancer Letters, New York, USA, vol. 158, N° 1, Jan. 1, 2000, pages 53-59.

Plants belonging to the family of Berberidaceae (*Berberis vulgaris, Berberis aristata*, other species of *Berberis*, and *Mahonia aquifolium*) contain active substances such as berberine and berbamine. The former inhibits chemoresistance and radioresistance, neoangiogenesis and telomerase; it has an anti-hypercholesterolerric, antidiabetic and cardioprotective effect. However, it has a serious drawback in that it may induce MDR (multidrug resistance). To counter this undesirable effect, it is possible to use berbamine, which, in addition to the cardioprotective effect already mentioned for berberine, shows a specific anti-tumor effect towards MDR and an antiarrhythmic effect. See also the paper published in Alternative and Complementary Therapies, Mary Ann Liebert, Larchmont, New York, USA. Vol 8, N° E, Jan. 12, 2002, pages 336-340, which sums up the knowledge about the use of plants containing berbamine to counter MDR. The cytotoxic effect of the fruit of *Berberis vuigaris* has been described in Int. J. Cancer Res. (Vol 2, No 1, 2006, pages 1-9).

Plants belonging to the family of Papaveraceae (*Eschscholzia caufomica, Macleaya cordata* or *Bocconia frutescens*) contain chelerythrine and sanguinarine. The plant or an extract thereof can also be *harpagophytum procumbens*. Chelerythrine has an inhibitory effect on the production of TNF-alpha: this effect, although unsuitable for tumors at an early stage, is however valuable at a pre-terminal and terminal stage, since it suppresses anorexia, cachexia and hyperalgesia, which are typical in pre-terminal and terminal stage oncological patients. Moreover, chelerythrine reduces mitochondrial respiration, which is known to be already poor in the mitochondria of tumor cells. Sanguinarine inhibits both NF-kB and AP-1 [Biochem. Pharmacol. 2004 Sep. 15; 68(6): 1101-11]: both are usually quiescent factors that are activated as a result of exposure to anti tumor antiblastics or to ionizing radiation. The preparation of anti-tumor extracts of *Macleaya cordata* or *Chelidonium majus* (a plant that is not admitted as a food supplement) containing chelerythrine is described in CN 1470513. The anti-tumour activity of benzophenanthridine alkaloids such as chelerythrine and sanguinarine, and of protoberberine alkaloids such as berberine is also described in Planta Medica, Vol 69(2), Jan. 2, 2003, pages 97-108.

The active ingredients can be present in a substantially pure and isolated form or in the form of at least three different extracts of plants, one belonging to the family of Asteraceae, one belonging to the family of Berberidaceae and one belonging to the family of Papaveraceae.

The plants belonging to the family of Asteraceae are preferably *Arctium lappa, Cnicus benedictus* and *Saussurea medusa*.

The plants belonging to the family of Berberidaceae are preferably *Berberis vulgaris, Berberis aristata* and *Mahonia aquifolium*.

The plants belonging to the family of Papaveraceae are preferably selected from the group comprising *Eschscholzia californica, Macleaya cordata* and *Bocconia frutescens*.

An object of the present invention is a combination comprising or, alternatively, consisting of: (i) at least one compound selected from the group comprising or, alternatively, consisting of rutin, oxerutin, diosmin, troxerutin and hesperidin; and/or (ii) melatonin; and/or (iii) chemotherapeutic agents; and/or (iv) at least one compound selected from the group comprising or, alternatively, consisting of arctigenin, arctiin, berberine, berbamine, sanguinarine and chelerythrine, as such or in the form of plant extracts containing said compounds; for use in the treatment of neoplasias and the prevention/suppression of chemoresistance to antiblastics and/or radioresistance to radiotherapy. Preferably, the combination comprising or, alternatively, consisting of: (i) at least one compound selected from the group comprising or, alternatively, consisting of rutin, oxerutin, diosmin, troxerutin and hesperidin; (ii) melatonin; (iii) cyclophosphamide and methotrexate); and/or (iv) at least one compound selected from the group comprising or, alternatively, consisting of arctigenin, arctiin, berberine, berbamine, sanguinarine and chelerythrine, as such or in the form of plant extracts containing said compounds.

According to a preferred embodiment, the combination of the present invention comprises or, alternatively, consists of: (i) rutin; (ii) melatonin; (iii) cyclophosphamide and methotrexate and optionally (iv) the compounds arctigenin, arctiin, berberine, berbamine, sanguinarine and chelerythrine, as such or in the form of plant extracts containing said compounds.

Preferably, the combinations of the present invention further comprise at least one compound selected from the group comprising or, alternatively, consisting of apigenin, asparagus (ursolic acid), curcumin, lycopene, chili pepper (capsaicin), resveratrol, green tea (Camellin B) and *Uncaria* sspp.

According to a preferred aspect, the compositions of the invention, in addition to at least one flavonoid, preferably selected from the group comprising or, alternatively, consisting of oxerutin, diosrnin, hesperidin, troxerutin and rutin, in association with chemotherapeutic agents, preferably comprising cyclophosphamide and methotrexate, will contain extracts derived from:

a) *Arctium lappa*, in particular from the seeds;
b) *Berveris vulgaris*;
c) *Eschscholzia californica*.

According to a preferred aspect, the extracts derived from each plant belonging to the different families will be present in a proportion comprised between 20% and 60%.

The daily doses of the compounds isolated from the extracts will normally be included in the following ranges:

arctigenin and arctiin: 0.1-1.0 g per day
berberine and berbamine: 0.1-1.0 g per day
sanguinarine and chelerythrine: 0.01-0.250 g per day, preferably 0.020-0.150 g per day
rutin: 0.1-0.2 g per day.

According to the invention, the extracts of plants used can be in the form of an oily macerate, alcoholic extract, dry extract (obtained by extraction with ethanol or with methanol or with supercritical $CO_2$), fluid extract or mother tincture.

The compositions of the invention can be used as food supplements, suitably formulated for oral administration, and will be prepared according to conventional methods well known in the pharmaceutical field, such as those described in "Remington's Pharmaceutical Handbook", Mack Publishing Co., N.Y., USA, using excipients, diluents, filling agents and anti-caking agents that are acceptable for their final use. Examples of formulations of food supplements will be soft capsules (sealed, liquid-containing capsules) or semi-rigid or rigid capsules (with a two-part coating, containing powder or granules), pastilles, tablets, wafers, granulates, single-dose sachets of powder, syrups and vials.

In order to improve bioavailability, it is preferable that at least one of the components of the composition be in a micronized form. The micronized compounds are prepared using conventional methods that are well known in the pharmaceutical field. Preferably, in the micronized compounds, the average diameter of the particles is less than 10

μm; more preferably the average diameter of the particles is less than 5 μm and even more preferably it is less than 1 μm.

The activity of the association of at least one flavonoid with synthetic chemotherapeutic agents (cyclophosphamide/methotrexate) and/or arctigenin, arctiin, berberine, berbamine, sanguinarine and chelerythrine (indicated with the term "Extracts" in the Tables) was studied in resistant cell lines of adenocarcinomas and carcinomas in comparison with chemosensitive tumour cell lines and line cells.

An object of the present invention is a composition comprising a mixture which comprises or, alternatively, consists of: rutin, preferably at a concentration of 10 μM to 100 μM, for example 20, 30, 40 and 50 μM; cyclophosphamide and/or methotrexate, preferably at a concentration of 500 to 1500 ng/ml, preferably 850 ng/ml, 1000 ng/ml, or 1300 ng/ml.

In particular, chemoresistant human tumour cells MDA-MB-231 (breast adenocarcinoma), ECV-304 (bladder carcinoma), HuH-7 (hepatocellular carcinoma) and HTB-43 (squamous cell carcinoma of the pharynx), chemosensitive tumour cells MCF-7 (breast adenocarcinoma) and non-tumoral healthy human mammal fibroblasts (HMF) were used.

The results, shown in Tables 1-3, demonstrate a directly proportional, though not linear, relationship between the resistance of tumor cells to the chemotherapeutic agent and the effectiveness of the chemotherapeutic agent associated with the extract and/or with the flavonoid

TABLE 1

| Treatment | Cell viability (%) | | |
|---|---|---|---|
| | MDA-MB-231 | MCF-7 | HMF |
| Control | 100 | 100 | 100 |
| Cyclophosphamide 1300 ng/mL | 89 | 8.6 | 42 |
| Cyclophosphamide 1000 ng/mL | 93 | 7.5 | 48 |
| Cyclophosphamide 850 ng/mL | 96 | 6.9 | 54 |
| Extracts 850 ng/mL | 94 | 5 | 82 |
| Extracts 650 ng/mL | 100 | 8 | 84 |
| Extracts 450 ng/mL | 100 | 12 | 92 |
| Rutin 100 μM | 51 | 4 | 86 |
| Rutin 50 μM | 58 | 5 | 88 |
| Rutin 20 μM | 66 | 8 | 92 |

TABLE 2

| Treatment | Cell viability (%) MDA-MB-231 |
|---|---|
| Extracts 650 ng/mL + Cyclophosphamide 850 ng/mL | 58 |
| Rutin 50 μM + Cyclophosphamide 850 ng/mL | 11 |
| Extracts 650 ng/mL + Rutin 50 μM | 16 |
| Extracts 650 ng/mL + Rutin 50 μM + Cyclophosphamide 850 ng/mL | 3 |

TABLE 3

| Treatment | Cell viability (%) | | |
|---|---|---|---|
| | ECV-304 | HuH-7 | HTB-43 |
| Control | 100 | 100 | 100 |
| Cyclophosphamide 850 ng/mL | 70 | 58 | 36 |
| Extracts 650 ng/mL | 24 | 74 | 24 |
| Rutin 50 μM + Cyclophosphamide 850 ng/mL | 17 | 46 | 21 |
| Extracts 650 ng/mL + Rutin 50 μM + Cyclophosphamide 850 ng/mL | 12 | 32 | 12 |

Table 4 below shows data obtained for MDA-MB-231 cells with quercetin, the aglycone of rutin, alone or in association with cyclophosphamide. The absence of synergistic effects appears evident, unlike what was found with rutin.

TABLE 4

| Treatment | Cell viability (%) MDA-MB-231 |
|---|---|
| Quercetin 100 μM | 76 |
| Quercetin 50 μM | 81 |
| Quercetin 20 μM | 91 |
| Quercetin 100 μM + Cyclophosphamide 850 ng/mL | 62 |
| Quercetin 50 μM + Cyclophosphamide 850 ng/mL | 66 |
| Quercetin 20 μM + Cyclophosphamide 850 ng/mL | 79 |

TABLE 5

The viability of chemoresistant MDA-MB-231 human tumor cells (breast adenocarcinoma) was measured 24, 48 and 72 hours after treatment with the specified compounds.

| | Treatment | 24 h | 48 h | 72 h |
|---|---|---|---|---|
| 1 | Control (no treatment) | 100 | 100 | 100 |
| 2 | Cyclo (20 μM) + Metho (2 μM) + Rutin (50 μM) | 16.18 ± 0.79 | 9.69 ± 0.57 | 4.59 ± 0.77 |
| 3 | Cyclo (20 μM) + Metho (2 μM) + Rutin (50 μM) + Melatonin (1 mM) | 10.70 ± 0.73 | 7.46 ± 0.43 | 4.06 ± 0.49 |
| 4 | Cyclo (10 μM) + Metho (1 μM) + Rutin (50 μM) | 20.73 ± 0.96 | 10.78 ± 0.87 | 6.18 ± 0.47 |
| 5 | Cyclo (10 μM) + Metho (1 μM) + Rutin (50 μM) + Melatonin (1 mM) | 13.59 ± 0.86 | 9.65 ± 0.68 | 5.03 ± 0.75 |
| 6 | Cyclo (20 μM) + Metho (2 μM) + Rutin (20 μM) + Melatonin (10 mM) | 4.58 ± 0.35 | 3.46 ± 0.27 | 2.95 ± 0.38 |
| 7 | Cyclo (10 μM) + Metho (1 μM) + Rutin (20 μM) + Melatonin (10 mM) | 4.31 ± 0.56 | 3.35 ± 0.36 | 3.08 ± 0.45 |

In table 5 the compound cyclo corresponds to cyclophosphamide, whilst the compound metho corresponds to methotrexate.

Test conditions: $5 \times 10^3$ cells; xCELLigence assay.

TABLE 6

The viability of chemosensitive MCF-7 tumor cells (breast adenocarcinoma) was
measured 24, 48 and 72 hours after treatment with the specified compounds.

| Treatment | 24 h | 48 h | 72 h |
|---|---|---|---|
| Control (no treatment) | 100 | 100 | 100 |
| Cyclo (20 µM) + Metho (2 µM) + Rutin (50 µM) | 12.68 ± 0.61 | 8.24 ± 0.49 | 3.69 ± 0.62 |
| Cyclo (20 µM) + Metho (2 µM) + Rutin (50 µM) + Melatonin (1 mM) | 9.32 ± 0.59 | 6.83 ± 0.68 | 2.67 ± 0.49 |
| Cyclo (10 µM) + Metho (1 µM) + Rutin (50 µM) | 14.43 ± 0.62 | 9.75 ± 0.29 | 4.06 ± 0.38 |
| Cyclo (10 µM) + Metho (1 µM) + Rutin (50 µM) + Melatonin (1 mM) | 10.63 ± 0.73 | 7.04 ± 0.37 | 2.86 ± 0.45 |
| Cyclo (20 µM) + Metho (2 µM) + Rutin (20 µM) + Melatonin (10 mM) | 3.79 ± 0.39 | 2.34 ± 0.46 | 2.05 ± 0.24 |
| Cyclo (10 µM) + Metho (1 µM) + Rutin (20 µM) + Melatonin (10 mM) | 4.02 ± 0.46 | 2.79 ± 0.34 | 2.53 ± 0.31 |

In table 6 the compound cyclo corresponds to cyclophosphamide, whilst the compound metho corresponds to methotrexate.
Test conditions: $5 \times 10^3$ cells; xCELLigence assay.

Table 7 shows that the combination of cyclophosphamide 40 µM+methotrexate 4 µM reduces cell viability to a value of 0.16±0.04% with respect to an untreated control group; the addition of rutin at a concentration of 100 µM and 50 µM induces no statistically relevant difference.

TABLE 7

Cell viability of MDA-MB-231 cells after 7 days of treatment
with different drug combinations; the results correspond to
average values obtained in 4 independent experiments.

| Treatment | Cell viability % |
|---|---|
| Control (no treatment) | 100 |
| Cyclo (40 µM) + Metho (4 µM) | 0.16 ± 0.04 |
| Cyclo (40 µM) + Metho (4 µM) + Rutin (100 µM) | 0.33 ± 0.13 |
| Cyclo (40 µM) + Metho (4 µM) + Rutin (50 µM) | 1.10 ± 0.21 |

Table 8 shows that the combination of cyclophosphamide 20 µM+methotrexate 2 µM reduces cell viability to a value of 24.80±0.6% with respect to an untreated control group, whereas the addition of 20 µM of rutin further reduces cell viability. Similar results were obtained with concentrations of cyclophosphamide and methotrexate of 10 µM and 1 µM, respectively. In general, the presence of the flavonoid results in an increase of about 10% of the anti-tumor activity of the combination of chemotherapeutic agents.

TABLE 8

Cell viability of MDA-MB-231 cells after 7 days of treatment
with different drug combinations; the results correspond to
average values obtained in 4 independent experiments.

| Treatment | Cell viability % |
|---|---|
| Control (no treatment) | 100 |
| Cyclo (40 µM) + Metho (4 µM) | 0.16 ± 0.04 |
| Cyclo (20 µM) + Metho (2 µM) | 24.80 ± 0.6 |
| Cyclo (20 µM) + Metho (2 µM) + Rutin (20 µM) | 12.61 ± 0.87 |
| Cyclo (10 µM) + Metho (1 µM) | 29.15 ± 1.18 |
| Cyclo (10 µM) + Metho (1 µM) + Rutin (20 µM) | 19.87 ± 1.34 |

TABLE 9

Cell viability of MDA-MB-231 cells after 7 days of treatment
with different drug combinations; the results correspond to
average values obtained in 4 independent experiments.

| Treatment | Cell viability % |
|---|---|
| Control (no treatment) | 100 |
| Cyclo (40 µM) | 1.07 ± 0.22 |
| Cyclo (40 µM) + Rutin (100 µM) | 0.47 ± 0.13 |
| Cyclo (40 µM) + Rutin (50 µM) | 0.88 ± 0.21 |

TABLE 10

Cell viability of MCF-7 cells after 7 days of treatment
with different drug combinations; the results correspond
to average values obtained in 4 independent experiments.

| Treatment | Cell viability % |
|---|---|
| Control (no treatment) | 100 |
| Cyclo (40 µM) + Metho (4 µM) | 0.75 |
| Cyclo (20 µM) + Metho (2 µM) | 1.71 |
| Cyclo (20 µM) + Metho (2 µM) + Rutin (20 µM) | 0.25 |
| Cyclo (10 µM) + Metho (1 µM) | 4.57 |
| Cyclo (10 µM) + Metho (1 µM) + Rutin (20 µM) | 1.46 |

The results obtained demonstrate that the flavonoids of the invention effectively increase the activity of the combination of methotrexate and cyclophosphamide against MDA-MB-231 cells. As a matter of fact, a statistically relevant reduction of cell viability was observed after the addition of the flavonoid to the different combinations of chemotherapeutic agents. It can therefore be inferred that the flavonoids of the present invention reduce the resistance of tumor cells to drugs.

In the above experiments, the combination of cyclophosphamide 40 µM and methotrexate 4 µM results in the highest reduction of cell viability. These concentrations correspond 10 mg/kg of cyclophosphamide and 1.5 mg/kg of methotrexate in humans, which are the maximum doses administered to patients with breast cancer metastases. However, as is known, this therapy induces serious adverse effects in patients. Therefore, the aim of the present invention is to reduce the concentrations of cyclophosphamide and methotrexate by means of an adjuvant therapy with a flavonoid. Experimental data demonstrate that the concentrations of cyclophosphamide and methotrexate, and as a result their adverse effects in patients suffering from tumors, can be reduced by adding a flavonoid to said combination.

Examples of preparation of the extracts used in the invention, as well as examples of compositions of the invention are set forth below.

EXAMPLE 1

Preparation of an Alcoholic Extract from Fresh Plants 530 grams consisting of the three plants together (each in a proportion of 20% to 60%) are placed in 1100 ml of an ethanol/water mixture (40% to 90% ethanol) and ground in a mixer. The resultant is left to "rest" for a period of 4 to 8 days, with care being taken to ensure that the ground plants remain submerged in the solution. At the end of this period the liquid part is poured off, the vegetable part is pressed and the liquids are collected and then filtered.

The extract thus obtained has a deep green-brownish color.

EXAMPLE 2

Preparation of an Alcoholic Extract from Dry Plants

An amount of thy plants comprised from 370 to 450 grams is used for 1200 ml of hydroalcoholic solution (40% to 90% ethanol). The resultant is left to "rest" for about two weeks. At the end of the impregnation/dyeing of the solvent, the liquid part is poured off, the vegetable part is pressed and the liquids are collected and then filtered.

The invention claimed is:

1. A method for treating a chemoresistant tumor in a subject, the method comprising
administering to the subject a composition comprising an effective amount of
at least one flavonoid selected from the group consisting of rutin, oxerutin, diosmin, troxerutin and hesperidin;
at least one chemotherapeutic agent comprising cyclophosphamide in a concentration ranging from 10 to 20 µM, and methotrexate, in a concentration ranging from 1 to 2 µM; and
melatonin in a concentration ranging from 1 mM to 10 mM,
wherein the at least one flavonoid is rutin having a concentration of 10 to 100 µM.

2. The method according to claim 1, wherein the at least one flavonoid is rutin.

3. The method according to claim 1, wherein said composition further comprises at least one compound selected from the group consisting of arctigenin, arctiin, berberine, berbamine, sanguinarine, chelerythrine and *harpagophytum procumbens*.

4. The method according to claim 1, wherein said composition further comprises at least one extract derived from:
a) a plant belonging to the family of Asteraceae selected from the group consisting of *Arctium lappa, Cnicus benedictus* and *Saussurea medusa;*
b) a plant belonging to the family of Berberidaceae selected from the group consisting of *Berberis vulgaris, Berberis aristata* and *Mahonia aquifolium;*
c) a plant belonging to the family of Papaveraceae, selected from the group consisting of *Eschscholzia californica, Macleaya cordata* and *Bocconia frutescens*, or d) *Harpagophytum procumbens* (devil's claw).

5. The method according to claim 1, wherein said composition further comprises at least one extract derived from:
a) *Arctium lappa;*
b) *Berberis vulgaris;* or
c) *Eschscholzia californica.*

6. The method according to claim 1, wherein the at least one flavonoid and/or the at least one chemotherapeutic agent is in a micronized form.

7. A method for the treatment of neoplasias and for the prevention/suppression of chemoresistance to antiblastics and/or radioresistance to radiothereapy in a subject, the method comprising
administering to the subject a composition comprising an effective amount of
at least one flavonoid selected from the group consisting of rutin, oxerutin, diosmin, troxerutin and hesperidin;
at least one chemotherapeutic agent comprising cyclophosphamide in a concentration ranging from 10 to 20 µM and methotrexate, in a concentration ranging from 1 to 2 µM; and
melatonin in a concentration ranging from 1 mM to 10 mM,
wherein the at least one flavonoid is rutin having a concentration of 20 to 50 µM,
and optionally administering to the subject at least one flavonoid selected from
the group consisting of arctigenin, actin, berberine, berbamine, sanguinarine, chelerythrine and *Harpagophytum procumbens.*

8. The method according to claim 1, wherein the chemoresistant tumor is a solid tumor.

9. The method according to claim 7, wherein the at least one compound is in the form of a plant extract.

10. The method according to claim 3, wherein the at least one compound is in the form of a plant extract.

11. The method according to claim 8, wherein the solid tumor is breast cancer.

12. A composition for the treatment of a chemoresistant tumor, the composition comprising an effective amount of
at least one flavonoid selected from the group consisting of rutin, oxerutin, diosmin, troxerutin and hesperidin;
at least one chemotherapeutic agent comprising cyclophosphamide in a concentration ranging from 10 to 20 µM and methotrexate, in a concentration ranging from 1 to 2 µM; and
melatonin in a concentration ranging from 1 mM to 10 mM.

13. The composition according to claim 12, wherein the at least one chemotherapeutic agent comprises cyclophosphamide and methotrexate.

14. The composition according to claim 12, wherein the at least one flavonoid is rutin.

15. The composition according to claim 12, wherein the chemoresistant tumor is a solid tumor.

16. The composition according to claim 12, wherein the at least one flavonoid is rutin having a concentration of 20 to 50 µM.

* * * * *